US00PP11031P

United States Patent [19]

Koppe

[11] Patent Number: Plant 11,031

[45] Date of Patent: Aug. 10, 1999

[54] BEGONIA PLANT NAMED 'ADA'

[75] Inventor: Lubbertus H. Koppe, Ermelo, Netherlands

[73] Assignee: Koppe Veredeling B.V., Ermelo, Netherlands

[21] Appl. No.: 09/004,809

[22] Filed: Jan. 9, 1998

[51] Int. Cl.[6] ..... A01H 5/00

[52] U.S. Cl. ..... Plt./344

[58] Field of Search ..... Plt./348, 343, 344

[56] References Cited

U.S. PATENT DOCUMENTS

P.P. 3,905 6/1976 Mikkelsen ..... Plt./349

P.P. 7,004 8/1989 Drewlow et al. ..... Plt./349

P.P. 9,504 4/1996 Koppe ..... Plt./349

OTHER PUBLICATIONS

GTITM UPOVROM Citation for 'ADA' Asper NL PBR 'BGN0232', Nov. 16, 1996.

*Primary Examiner*—Howard J. Locker
*Assistant Examiner*—Kent L. Bell
*Attorney, Agent, or Firm*—C. A. Whealy

[57] ABSTRACT

A distinct cultivar of Begonia plant named 'Ada', characterized by its large soft pink flowers that are about 6 to 7 cm in diameter; fully double flowers with numerous tepals per flower; upright and rounded plant form; and excellent post-production longevity.

3 Drawing Sheets

The present invention relates to a new and distinct cultivar of Begonia plant, botanically known as *Begonia×hiemalis,* commercially known as Elatior Begonia, and hereinafter referred to by the cultivar name 'Ada'.

The new cultivar was discovered by the inventor in a controlled environment in Ermelo, The Netherlands, in 1993, as a naturally-occurring mutation of the Begonia cultivar 'Azotus', disclosed in U.S. Plant Pat. No. 9,504. The new cultivar was observed as a single plant in a group of flowering plants of the parent cultivar. The selection of this plant was based on its soft pink flower color in contrast to the very dark pink flower color of the parent cultivar.

Asexual reproduction of the new cultivar by terminal cuttings taken in a controlled environment in Ermelo, The Netherlands, has shown that the unique features of this new Begonia are stable and reproduced true to type in successive generations.

The cultivar 'Ada' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Ada'. These characteristics in combination distinguish 'Ada' as a new and distinct cultivar:

1. Large soft pink flowers that are about 6 to 7 cm in diameter.
2. Fully double flowers with numerous tepals per flower.
3. Upright and rounded plant form.
4. Excellent postproduction longevity.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical flowering plant of 'Ada'.

The photograph on the second sheet comprises a close-up view of a typical flower. The photograph at the top of the third sheet comprises a close-up view of the upper surfaces of typical leaves at three stages of development (top) and typical flowers at five stages of development (lower).

The photograph at the bottom of the third sheet comprises a close-up view of the lower surfaces of typical leaves at three stages of development (top) and typical flowers at five stages of development (lower). Flower and foliage colors in the photographs may differ from the actual colors due to light reflectance and shadows.

DETAILED BOTANICAL DESCRIPTION

In the following description, color references are made to The Royal Horticultural Society Colour Chart except where general terms of ordinary dictionary significance are used. The following observations and measurements describe plants grown in Ermelo, The Netherlands, under commercial practice in a glass-covered greenhouse. Average day and night temperatures were 20° C. during the first three to four weeks then lowered to an average day and night temperature of 19° C. until flowering. Four weeks after planting, two weeks of long nyctoperiods were given followed by short nyctoperiods. Measurements and numerical values represent averages for typical flowering plants.

Botanical classification: *Begonia×hiemalis* 'Ada'.

Commerical classification: Elatior Begonia.

Parentage: Naturally-occuring mutation of *Begonia× hiemalis* cultivar 'Azotus', disclosed in U.S. Plant Pat. No. 9,504.

Propagation:

*Type.*—Terminal cuttings.

*Time to rooting.*—About 5 weeks with soil temperatures of 21° C.

*Rooting habit.*—Fine, fibrous and well-branched, plants do not form tubers.

Plant description:

*Plant form.*—Upright and rounded potted plant, freely branching with good stem and stem base strength. Flowers are fully double and abundant. Plants flower continuously.

*Growth habit.*—Moderate growth rate, vigorous. Suitable for 9 to 15 cm containers. Under optimal environmental and cultural conditions, usually 10 to 12 weeks are required to produce proportional 13-cm potted plants from terminal cuttings. Vegetative shoots are formed at basal nodes and flowering shoots are formed at upper nodes. Freely branching.

*Plant height.*—About 25 cm.

*Leaves.*—Arrangement: Simple, alternate. Length: About 12 cm. Width: About 13 cm. Shape: Asymmetrical, obliquely cordate, reniform. Apex: Acute. Base: Cordate, overlapping. Margin: Doubly serrate. Texture: Smooth, leathery. Color: Young and fully expanded foliage, upper surface: 147A. Young and fully expanded foliage, lower surface: 147B. Venation, upper and lower surfaces: 144D. Petiole: 144D.

Flower description:

*Flowering habit.*—Large and fully double flowers with numerous tepals arranged in axillary cymes. Usually four to six flowers per cyme. Many cymes in flower simultaneously. Flowering continuous.

*Natural flowering season.*—Plants will flower year round regardless of nyctoperiod, however plants flower earlier and more abundantly from mid-February until November in the Northern Hemisphere.

*Flowers.*—Shape: Rounded. Diameter: About 6 to 7 cm. Depth (height): About 3 cm.

*Flower buds.*—Length: About 2.5 cm. Diameter: About 1.25 cm. Color: 44D.

*Tepals.*—Arrangement: Rosette. Shape: Broadly cordate with rounded apex and crenate margin. Quantity per flower: Usually about 40 per flower. Length, largest tepals: About 3.5 cm. Width, largest tepals: About 4.25 cm. Texture: Smooth, satiny, glabrous. Color: When opening: 56D. Fully opened, upper and lower surfaces: Apices, initailly light pink, 56D, becoming slightly darker, 56B; base, dark pink, 58C.

*Peduncles.*—Angle: Rigid to bent. Length: About 7 to 9 cm. Texture: Glabrous. Color: 144D.

*Pedicels.*—Angle: About 40° to 45° to peduncle. Length: About 2.5 cm to 3 cm. Texture: Glabrous. Color: 144D, with slight anthocyanin.

*Flower bracts.*—Arrangement: Two, opposite. Shape: Very broadly cordate. Margin: Serrate. Color: 144C/144D.

*Reproductive organs.*—Stamens: None observed. Pistils: None observed.

Postproduction longevity:

*Individual flowers.*—Generally about 2 to 3 weeks.

*Whole plants.*—About 6 weeks under interior conditions.

Disease resistance: Resistance to diseases common to Begonia has not been noted.

Seed production: Seed production has not been observed as reproductive organs are not formed.

It is claimed:

1. A new and distinct cultivar of Begonia plant named 'Ada', as illustrated and described.

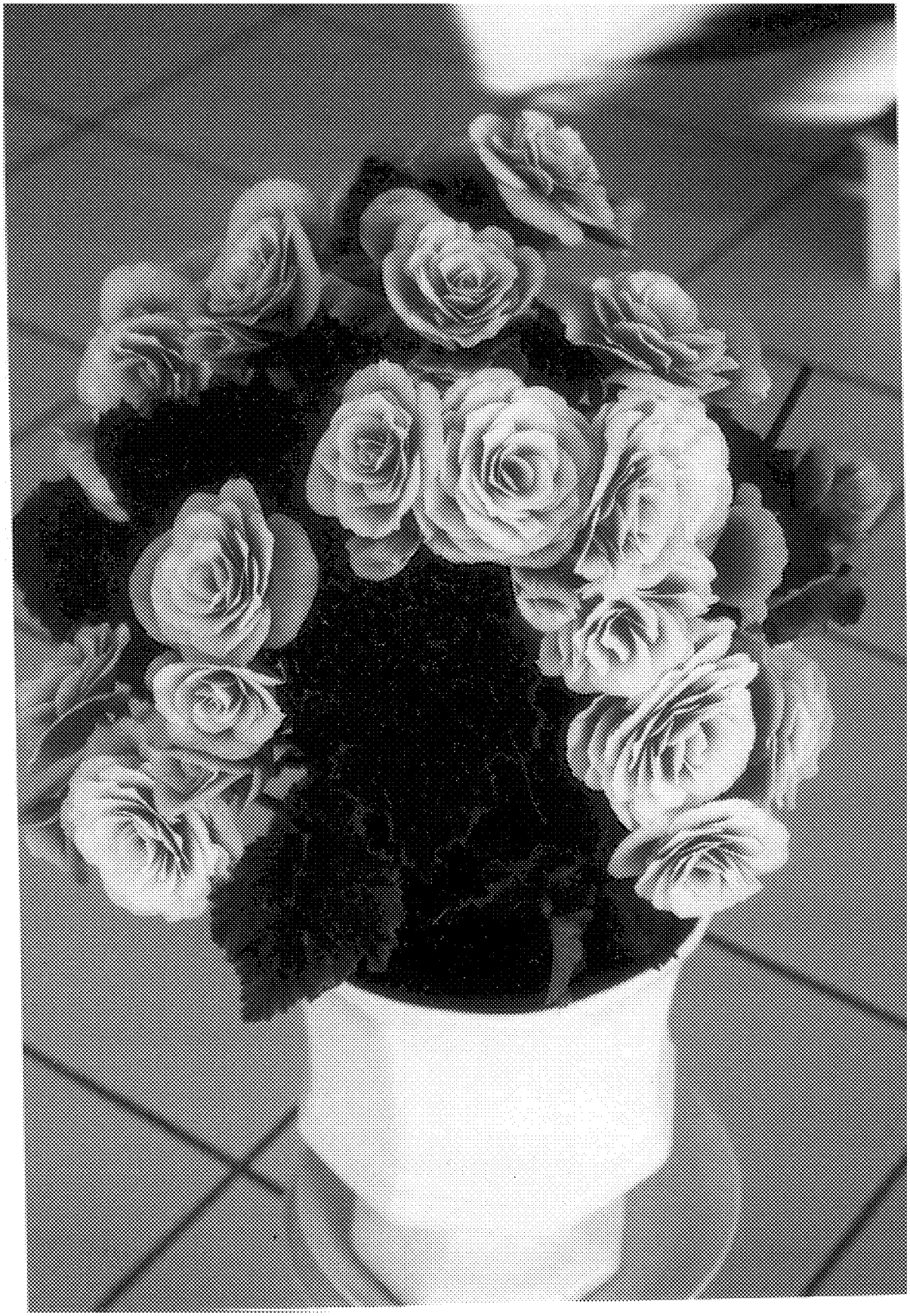

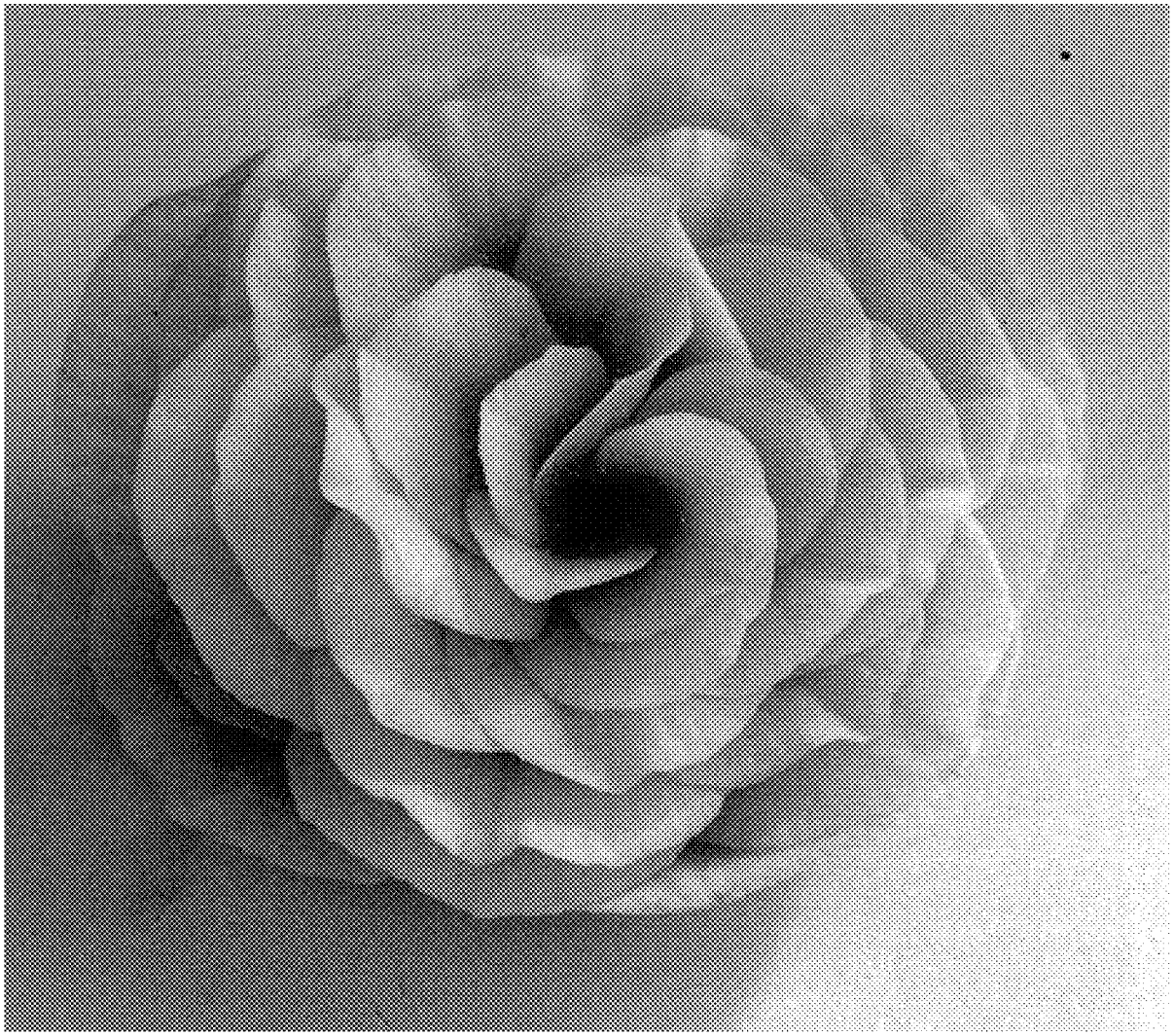

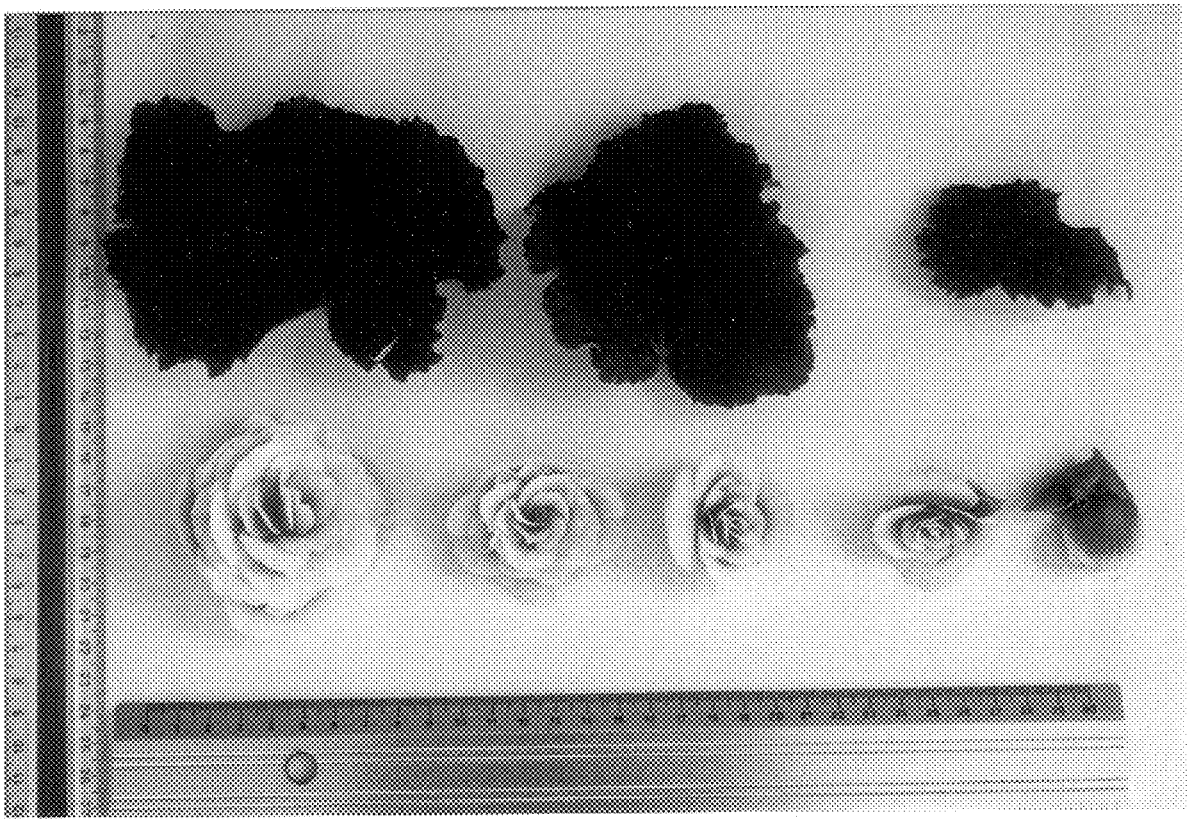
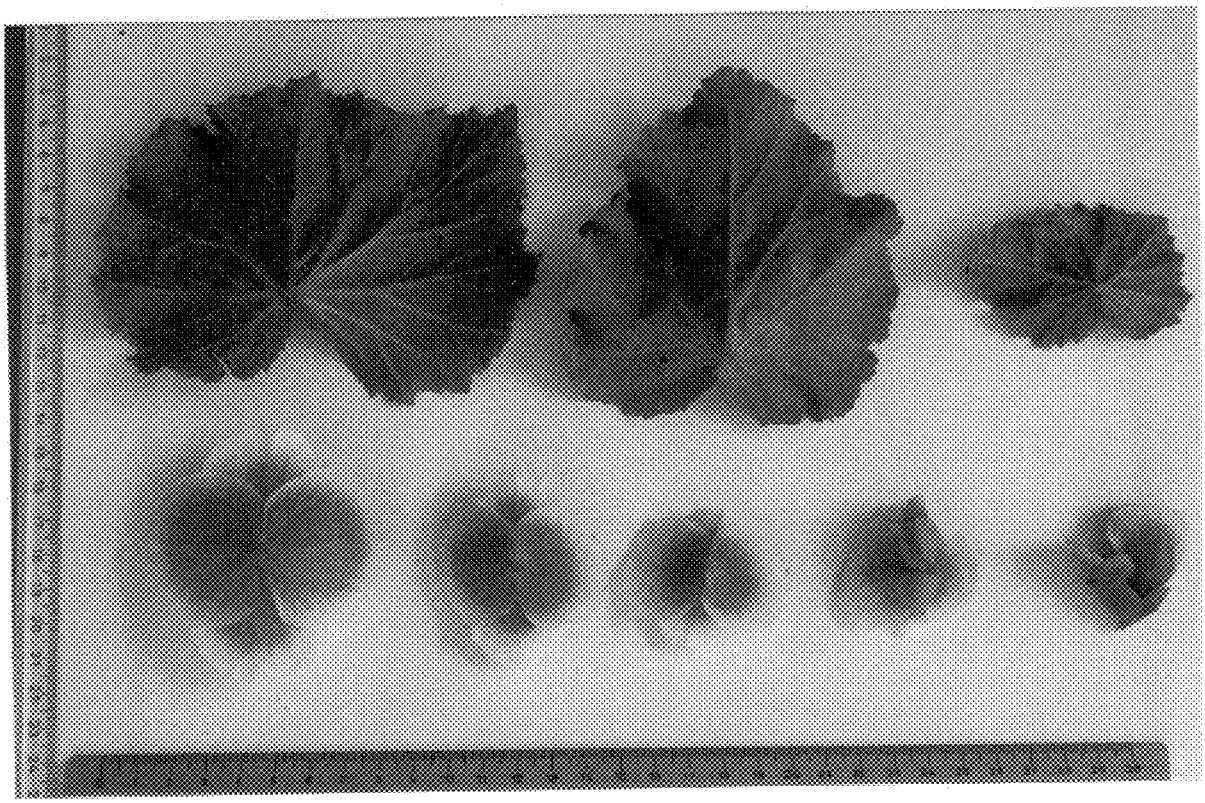

* * * * *